(12) United States Patent
Zuo et al.

(10) Patent No.: US 11,857,551 B1
(45) Date of Patent: Jan. 2, 2024

(54) METHODS FOR THE PREVENTION AND TREATMENT OF HEARING LOSS

(71) Applicant: Ting Therapeutics LLC, Omaha, NE (US)

(72) Inventors: Jian Zuo, Omaha, NE (US); Pezhman Salehi Dermanaki, Elkhorn, NE (US)

(73) Assignee: Ting Therapeutics LLC, Omaha, NE (US)

( * ) Notice: Subject to any disclaimer, the term of this patent is extended or adjusted under 35 U.S.C. 154(b) by 272 days.

(21) Appl. No.: 17/371,847

(22) Filed: Jul. 9, 2021

Related U.S. Application Data

(60) Provisional application No. 63/050,568, filed on Jul. 10, 2020.

(51) Int. Cl.
| | | |
|---|---|---|
| *A61K 31/517* | (2006.01) | |
| *A61K 45/06* | (2006.01) | |
| *A61K 31/513* | (2006.01) | |
| *A61F 11/00* | (2022.01) | |

(52) U.S. Cl.
CPC .......... *A61K 31/517* (2013.01); *A61F 11/00* (2013.01); *A61K 31/513* (2013.01); *A61K 45/06* (2013.01)

(58) Field of Classification Search
CPC ..... A61F 11/00; A61K 31/517; A61K 31/513; C07C 59/88
See application file for complete search history.

(56) References Cited

U.S. PATENT DOCUMENTS

| | | |
|---|---|---|
| 6,268,351 B1 | 7/2001 | Oberholtzer et al. |
| 6,331,289 B1 | 12/2001 | Klaveness et al. |
| 6,448,283 B1 | 9/2002 | Ylikoski et al. |
| 6,680,047 B2 | 1/2004 | Klaveness et al. |
| 6,822,097 B1 | 11/2004 | Norman et al. |
| 7,427,608 B2 | 9/2008 | Nicotera et al. |
| 7,491,791 B2 | 2/2009 | Cody et al. |
| 8,211,656 B2 | 7/2012 | Hyde et al. |
| 8,329,683 B2 | 12/2012 | Chen et al. |
| 8,357,385 B2 | 1/2013 | Laronde et al. |
| 8,420,595 B2 | 4/2013 | Kopke et al. |
| 9,295,673 B2 | 3/2016 | Ren et al. |
| 9,353,150 B2 * | 5/2016 | Movassaghi ......... C07D 513/22 |
| 9,475,854 B2 | 10/2016 | Coffin et al. |
| 9,493,482 B2 | 11/2016 | Simon et al. |
| 9,682,141 B2 | 6/2017 | Jessen et al. |
| 9,987,244 B2 | 6/2018 | Gjorstrup |
| 10,004,701 B2 | 6/2018 | Dunman et al. |
| 10,010,585 B2 | 7/2018 | Stankovic et al. |
| 10,105,356 B2 | 10/2018 | Surber |
| 10,118,927 B2 | 11/2018 | Brown et al. |
| 10,183,964 B2 | 1/2019 | Sichtnik |
| 10,201,540 B2 | 2/2019 | Loose et al. |
| 10,213,511 B2 | 2/2019 | Loose et al. |
| 10,286,069 B2 | 5/2019 | Mannick et al. |
| 10,323,001 B2 | 6/2019 | Hangauer, Jr. et al. |
| 10,385,106 B2 | 8/2019 | Fougerolles et al. |
| 10,391,168 B1 | 8/2019 | Riether et al. |
| 10,441,616 B2 | 10/2019 | Park et al. |
| 10,555,915 B2 | 2/2020 | Kopke et al. |
| 10,583,140 B2 | 3/2020 | Tai et al. |
| 10,603,295 B2 | 3/2020 | Edge et al. |
| 10,689,388 B1 | 6/2020 | Castro et al. |
| 10,759,796 B2 | 9/2020 | Bourque et al. |
| 10,772,975 B2 | 9/2020 | Bancel et al. |
| 10,857,161 B2 | 12/2020 | McCall et al. |
| 10,874,743 B2 | 12/2020 | Mainolfi et al. |
| 10,947,213 B1 | 3/2021 | Sherer et al. |
| 10,973,834 B2 | 4/2021 | Manfredi et al. |
| 10,980,889 B1 | 4/2021 | Pitzen et al. |
| 10,987,356 B2 | 4/2021 | Zhao et al. |
| 10,988,477 B2 | 4/2021 | Bayly et al. |
| 11,000,540 B1 | 5/2021 | Siamon |
| 11,026,963 B2 | 6/2021 | Gallop et al. |
| 2003/0004351 A1 | 1/2003 | Davis et al. |
| 2006/0025406 A1 * | 2/2006 | Zembower ........... C07D 239/95 514/218 |
| 2006/0148829 A1 | 7/2006 | Meijer et al. |
| 2007/0078177 A1 | 4/2007 | Bao |
| 2007/0248690 A1 | 10/2007 | Trager |
| 2009/0130118 A1 | 5/2009 | Cohen |
| 2011/0002879 A1 | 1/2011 | Curry et al. |
| 2011/0305674 A1 | 12/2011 | Edge et al. |
| 2013/0085112 A1 | 4/2013 | Collard et al. |
| 2013/0225575 A1 | 8/2013 | Lichter et al. |
| 2014/0371213 A1 | 12/2014 | Berdini et al. |
| 2015/0050354 A1 | 2/2015 | Bouchon et al. |
| 2016/0089371 A1 | 3/2016 | Liu et al. |
| 2017/0189477 A1 | 7/2017 | Zuo et al. |
| 2018/0021315 A1 | 1/2018 | Zhang et al. |
| 2018/0291400 A1 * | 10/2018 | Zhang ..................... C12N 5/10 |
| 2019/0148067 A1 | 5/2019 | Hirata |

(Continued)

FOREIGN PATENT DOCUMENTS

| | | |
|---|---|---|
| WO | 0172298 A1 | 10/2001 |
| WO | 03076436 A1 | 9/2003 |

(Continued)

OTHER PUBLICATIONS

Hazlitt RA, Min J, Zuo J. Progress in the Development of Preventative Drugs for Cisplatin-Induced Hearing Loss. Jul. 12, 2018; 13; 61(13):5512-5524; J Med Chem. U.S.

(Continued)

*Primary Examiner* — Amanda L. Aguirre
(74) *Attorney, Agent, or Firm* — Susan B Fentress; Veritay Group IP PLLC

(57) ABSTRACT

Acquired hearing loss due to chemotherapy or noise exposure is a major health problem, and cisplatin chemotherapy often causes permanent hearing loss in cancer patients. However, there are no FDA-approved drugs for the treatment or prevention of cisplatin- or noise-induced hearing loss. In one aspect, use of compounds as an active agent to treat a hearing impairment and to prevent a hearing impairment, and methods of treating and/or preventing hearing impairments or disorders using the compositions are disclosed. This abstract is intended as a scanning tool for purposes of searching in the particular art and is not intended to be limiting of the present invention.

3 Claims, 25 Drawing Sheets

(56) References Cited

U.S. PATENT DOCUMENTS

| | | |
|---|---|---|
| 2019/0255090 A1 | 8/2019 | Zhang et al. |
| 2020/0031873 A1 | 1/2020 | çinarouglu et al. |
| 2020/0093923 A1 | 3/2020 | Zuo et al. |
| 2021/0030775 A1 | 2/2021 | Chen et al. |

FOREIGN PATENT DOCUMENTS

| | | |
|---|---|---|
| WO | 2007031098 A1 | 3/2007 |
| WO | 2009061345 A2 | 5/2009 |
| WO | 2011153348 A2 | 12/2011 |
| WO | 2012146936 A1 | 11/2012 |
| WO | 2013071415 A1 | 5/2013 |
| WO | 2013120107 A1 | 8/2013 |
| WO | 2014145205 A2 | 9/2014 |
| WO | 2016205806 A1 | 12/2016 |
| WO | 2017132530 A1 | 8/2017 |
| WO | 2018148071 | 9/2018 |
| WO | 2018204226 A1 | 11/2018 |
| WO | 2019210107 A1 | 10/2019 |
| WO | 2021087408 A1 | 5/2021 |

OTHER PUBLICATIONS

Yu D, Gu J, Chen Y, Kang W, Wang X, Wu H. Current Strategies to Combat Cisplatin-Induced Ototoxicity. Jul. 3, 2020; 22; 999; Front Pharmacol. U.S.

Alessi, Francesca et al.; The Cyclin-Dependent Kinase Inhibitors Olomoucine and Roscovitine Arrest Human Fibroblasts in G1 Phase by Specific Inhibition of CDK2 Kinase Activity; Experimental Cell Research; Nov. 25, 1998; 11 pages; 245, 8-18; Academic Press; U.S.

Kikkawa, Yayoi S. et al.; Hydrogen protects auditory hair cells from cisplatin-induced free radicals; Neurosci Lett. Sep. 5, 2014; 5 pages; 579:125-9; Elsevier; U.S.

Lasisi, Olawale Akeem et al.; Age-realted hearing loss, vitamin B12, and folate in the elderly; Otolaryngol Head Neck Surg. Dec. 2010; 5 pages; 143(6):826-30; Mosby, Inc.; U.S.

* cited by examiner

FIG. 8A
FIG. 8B
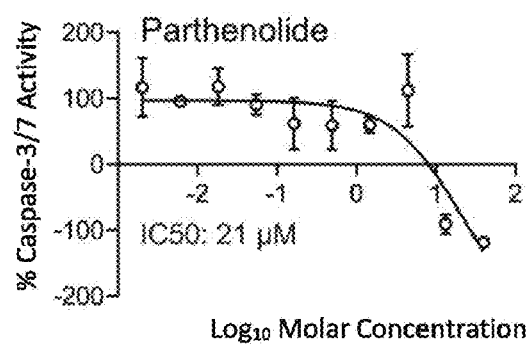
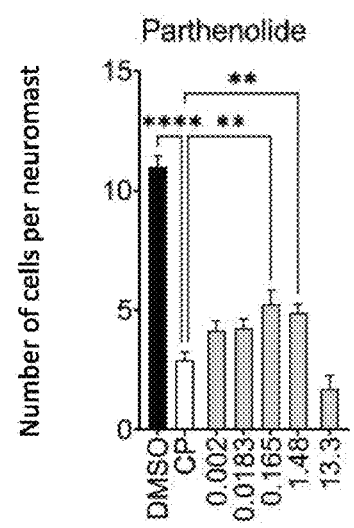

FIG. 9A
FIG. 9B
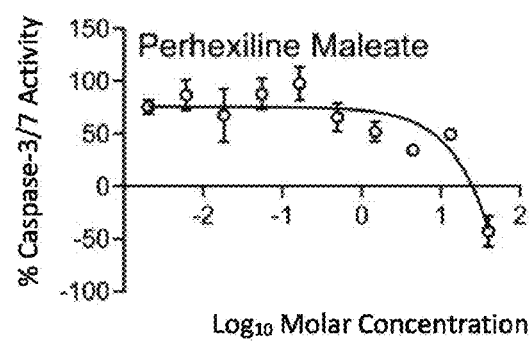
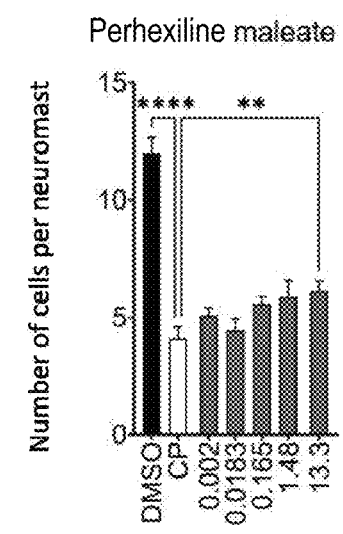

FIG. 10A
FIG. 10B
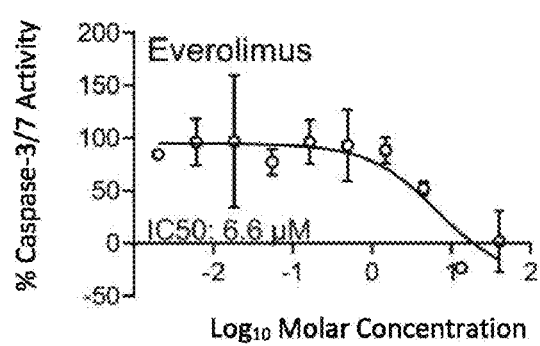
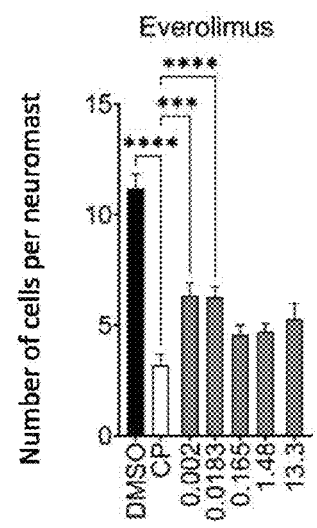

FIG. 11A
FIG. 11B
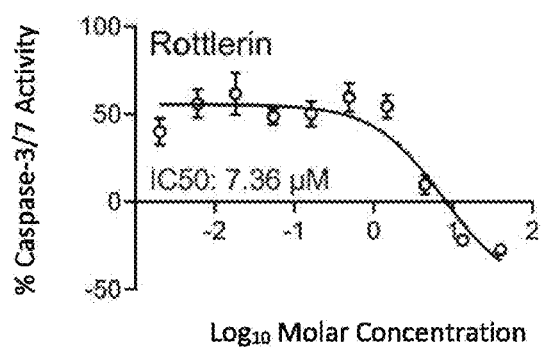
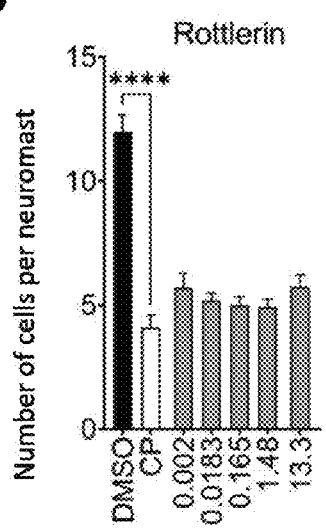

METHODS FOR THE PREVENTION AND TREATMENT OF HEARING LOSS

CROSS-REFERENCE TO RELATED APPLICATIONS

This application claims the benefit of U.S. provisional patent application Ser. No. 63/050,568 filed Jul. 10, 2020, under 35 USC § 119(e) and 35 U.S.C. § 111(a) (hereby specifically incorporated herein by reference).

STATEMENT REGARDING FEDERALLY SPONSORED RESEARCH OR DEVELOPMENT

NIH/NIDCD 1 R43 DC018762, NIH/NIDCD R01DC015444, NIH/NIDCD R01DC015010, Office of Naval Research (ONR) N00014-18-1-2507 and Department of Defense (DoD)/USAMRMC-RH170030. The government has certain rights in the invention.

BACKGROUND OF THE INVENTION

(1) Field of the Invention

The present invention relates to therapeutic uses of compounds for treating, inhibiting, and/or preventing loss of hearing.

(2) Description of Related Art Including Information Disclosed Under 37 CFR 1.97 and 37 CFR 1.98

Acquired hearing loss due to chemotherapy or noise exposure is a major health problem and cisplatin chemotherapy often causes permanent hearing loss in cancer patients. However, there are no FDA-approved drugs for the treatment or prevention of cisplatin- or noise-induced hearing loss. Platinum-based chemotherapy is a standard of care for various types of cancers, including ovarian, lung, testicular, and head and neck carcinoma. Cisplatin, one of the most effective platinum compounds, causes permanent hearing loss in 40-60% of treated cancer patients. One of the known mechanisms of cisplatin damage to the auditory sensory cells is DNA adduct formation leading to oxidative stress and cellular apoptosis. To reduce cisplatin damage to the inner ear cochlear cells, various therapeutic strategies including usage of antioxidants, anti-inflammatory agents, calcium channel blockers, kinase inhibitors, heat shock proteins, and thiol compounds as chemical deactivators have been used in previous studies. Sodium thiosulfate (STS), for example, has been shown effective in protecting hearing only in pediatric patients with localized hepatoblastoma who received cisplatin chemotherapy; however, it acts as a cisplatin chelator and is ineffective in protecting cisplatin-induced hearing loss (CIHL) in patients with other cancers.

There exists a need in the art for a solution to hearing loss due to noise, antibiotics, cisplatin during chemotherapy, or aging. Therapeutic methods described are a solution to problems in the art such as narrow therapeutic windows and safety margins and interference with cisplatin's antineoplastic activity.

BRIEF SUMMARY OF THE INVENTION

The invention provides a method to prevent or treat hearing loss including the steps of: administering to an animal in need thereof an effective amount of a pharmaceutical composition containing a therapeutically active agent, wherein the therapeutically active agent is selected by a process of determining overlaps in gene expression transcriptomic profiles between at least one of a plurality of cell-lines or mouse strains treated with ototoxic insults (cisplatin, noise or antibiotic exposure) and at least one of a plurality of cell-lines or mouse strains treated with one of the compounds. It is contemplated that the transcriptomic profile is a NIHL-resistant mouse strains to NIHL sensitive mouse strains (129SvJ and CAST); a transcriptomes of mice with dexamethasone treatment to those with treatment after noise exposure is a transcriptome perturbation of neonatal mouse organ of Corti exposed to gentamicin. The compounds include but are not limited to: DCPIB, importazole, 5-flurouracil, irinotecan, prothionamide, parthenolide, perhexiline maleate, rottlerin, chaetocin, thioridazine, radicicol, salermide, dimercaptopropanol, everolimus, raltitrexed, manumycin A, wortmannin, 6 mercaptopurine, Palbociclib, tiopronin, succimer, camptothecin, captopril, R406, AZD-7762, SB 218078, Crizotinib, LDN-193189, Daunorubicin, Mitomycin C, Geldanamycin, Luminepib, BMS-387032, CGP-60474, Alvocidib, PD-0325901, PD-184352, PD 98059, AZD-8330, Dovidtinib, BIBU 1361 Dihydrochloride, Canertinib, TWS119, AZD-8055, Torin-1, Torin-2, WYE-123132, PP 2, WZ-3105, HY-10247, Auranofin, 16-hydroxytiptolide, Withaferin-a, AS605240, ZSTK-474, Trichostatin A, PP-110, Akt inhibitor X, BML-257, A443654, Colforsin, P5172, Coumermycin A1, R08181, Tropisetron, Tofacitinib, Atracytlenolide, FLLL32, Zotiraciclib, Upadacitinib, Cerdulatinib, Baricitinib, Peficitinib, Levetiracetam, and Sinomenine.

The invention provides a method to prevent or treat hearing loss including the steps of administering to an animal in need thereof an effective amount of a pharmaceutical composition containing a therapeutically active agent, wherein the therapeutically active agent includes: DCPIB, importazole, 5-flurouracil, irinotecan, prothionamide, parthenolide, perhexiline maleate, rottlerin, chaetocin, thioridazine, radicicol, salermide, dimercaptopropanol, everolimus, raltitrexed, manumycin A, wortmannin, 6 mercaptopurine, Palbociclib, tiopronin, succimer, camptothecin, captopril, R406, AZD-7762, SB 218078, Crizotinib, LDN-193189, Daunorubicin, Mitomycin C, Geldanamycin, Luminepib, BMS-387032, CGP-60474, Alvocidib, PD-0325901, PD-184352, PD 98059, AZD-8330, Dovidtinib, BIBU 1361 Dihydrochloride, Canertinib, TWS119, AZD-8055, Torin-1, Torin-2, WYE-123132, PP 2, WZ-3105, HY-10247, Auranofin, 16-hydroxytiptolide, Withaferin-a, AS605240, ZSTK-474, Trichostatin A, PP-110, Akt inhibitor X, BML-257, A443654, Colforsin, P5172, Coumermycin A1, R08181, Tropisetron, Tofacitinib, Atracytlenolide, FLLL32, Zotiraciclib, Upadacitinib.

The inventive subject matter also includes a composition for use in preventing or treating hearing loss by protecting inner ear cells from death wherein the composition is an effective amount of: an active agent, wherein the active agent includes: DCPIB, importazole, 5-flurouracil, irinotecan, prothionamide, parthenolide, perhexiline maleate, rottlerin, chaetocin, thioridazine, radicicol, salermide, dimercaptopropanol, everolimus, raltitrexed, manumycin A, wortmannin, 6 mercaptopurine, Palbociclib, tiopronin, succimer, camptothecin, captopril, R406, AZD-7762, SB 218078, Crizotinib, LDN-193189, Daunorubicin, Mitomycin C, Geldanamycin, Luminepib, BMS-387032, CGP-60474, Alvocidib, PD-0325901, PD-184352, PD 98059, AZD-8330, Dovidtinib, BIBU 1361 Dihydrochloride, Canertinib, TWS119, AZD-8055, Torin-1, Torin-2, WYE- 123132, PP 2, WZ-3105, HY-10247, Auranofin, 16-hydroxytiptolide, Withaferin-a, AS605240, ZSTK-474, Trichostatin A, PP-110, Akt inhibitor X, BML-257, A443654, Colforsin, P5172, Coumermycin A1, R08181, Tropisetron, Tofacitinib, Atracytlenolide, FLLL32, Zotiraciclib, Upadacitinib, Cerdulatinib, Baricitinib, Peficitinib, Levetiracetam, and Sinomenine.or a pharmaceutically acceptable salt thereof. In one embodiment, the active agent includes: DCPIB, importazole, 5-flurouracil, irinotecan, prothionamide, parthenolide, perhexiline maleate, rottlerin, chaetocin, thioridazine, radicicol, salermide, dimercaptopropanol, everolimus, raltitrexed, manumycin A, wortmannin, 6 mercaptopurine, Palbociclib, tiopronin, succimer, camptothecin, and captopril.

The inventive subject matter also includes a kit made of: an active agent, wherein the active agent includes: DCPIB, importazole, 5-flurouracil, irinotecan, prothionamide, parthenolide, perhexiline maleate, rottlerin, chaetocin, thioridazine, radicicol, salermide, dimercaptopropanol, everolimus, raltitrexed, manumycin A, wortmannin, 6 mercaptopurine, Palbociclib, tiopronin, succimer, camptothecin, and captopril, or a pharmaceutically acceptable salt thereof; and one or more of: (A) at least one chemotherapeutic agent; (B) an antibiotic and (C) instructions for preventing a hearing impairment.

One novel aspect of the inventive subject matter is protecting the inner ear cells from death caused by noise, wherein the active agent is selected from the group consisting of: importazole and 5-flurouracil. Here this is accomplished by administering to an animal in need thereof an effective amount of a pharmaceutical composition containing a therapeutically active agent, wherein the therapeutically active agent includes: importazole and 5-flurouracil.

BRIEF DESCRIPTION OF THE SEVERAL VIEWS OF THE DRAWING

FIG. 8A shows parthenolide protects against CIHL.
FIG. 8B shows parthenolide protects against cisplatin ototoxicity.
FIG. 9A shows perhexine maleate protects against CIHL
FIG. 9B shows perhexine maleate protects against cisplatin ototoxicity.
FIG. 10A shows everolimus protects against CIHL.
FIG. 10B shows everolimus protects against cisplatin ototoxicity.
FIG. 11A shows rottlerin protects against CIHL.
FIG. 11B shows rottlerin protects against cisplatin ototoxicity.

DETAILED DESCRIPTION OF THE INVENTION

The present invention can be understood more readily by reference to the following detailed description of the invention and the examples included therein. Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

Figure 1:
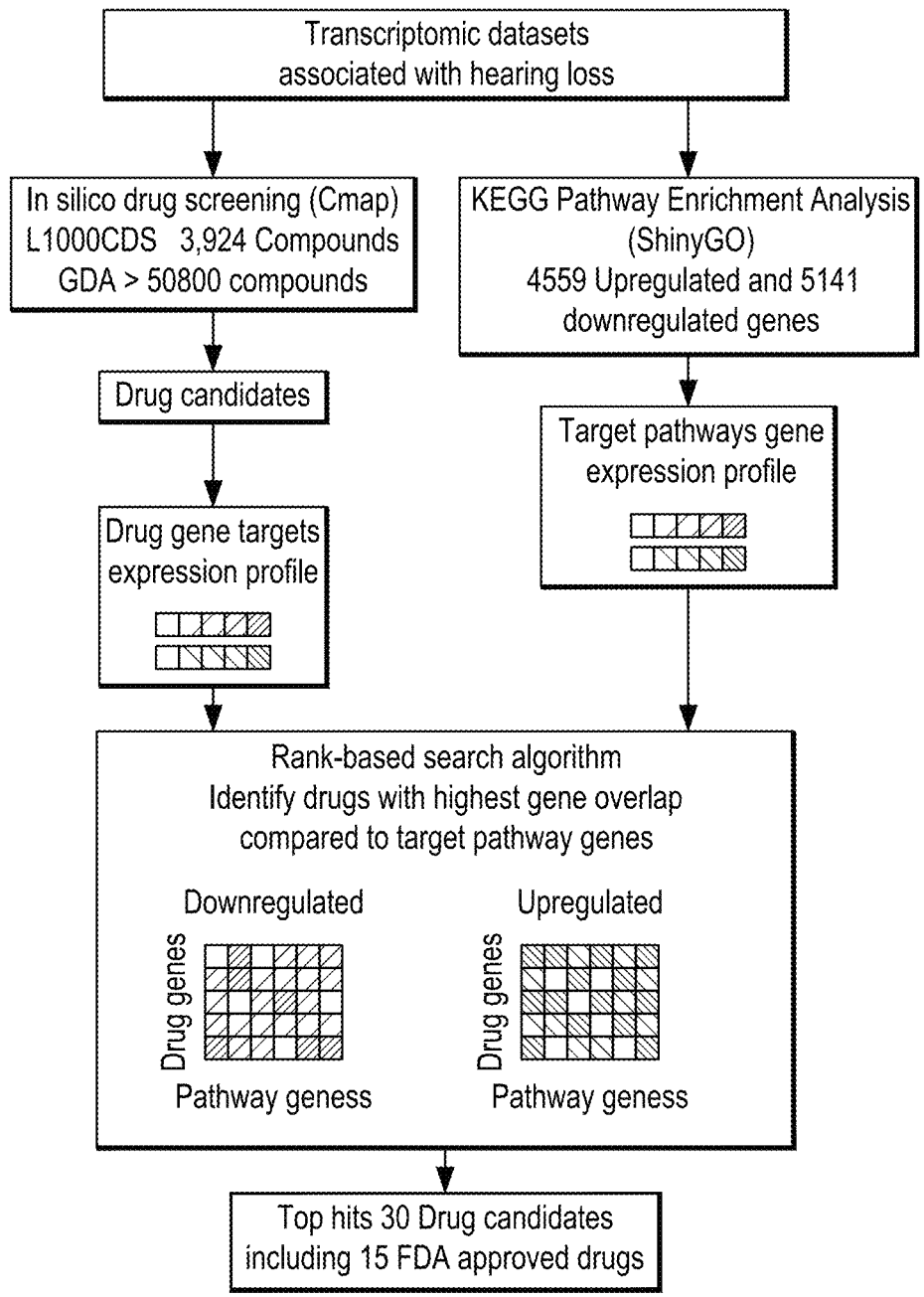
FIG. 1 is a schematic diagram showing how compounds of this invention were identified based on a comparison of data sets from drug screen connectivity maps and pathway enrichment analysis revealing drugs acting against hearing loss.

Now referring to FIG. 1 compounds were identified based on a comparison of data sets from drug screen connectivity maps and pathway enrichment analysis revealing compounds acting against hearing loss. This method was developed to derive drug candidates from a diverse chemical space, covering a wide range of biological pathways, avoiding bias associated with focusing on previously reported pathways. The resulting compounds exhibited overlaps in gene expression transcriptomic profiles between at least one of a plurality of cell-lines or mouse strains treated with ototoxic insults (cisplatin, noise or antibiotic exposure such as aminoglycoside) and at least one of a plurality of cell-lines or mouse strains treated with one of the compounds.

Here specifically, the data set sought was conformity to a NIHL-resistant mouse strains to NIHL sensitive mouse strains (129SvJ and CAST). Here specifically the data set sought was conformity to cisplatin-resistant and sensitive cancer cell lines, HEI-OC1 cell line, in vivo mouse cochlear single cell RNA seq with and without cisplatin treatment. Transcriptome perturbation of neonatal mouse organ of Corti exposed to gentamicin for damage related to antibiotic treatment. These compounds with an overlap of the data sets include: DCPIB, importazole, 5-flurouracil, irinotecan, prothionamide, parthenolide, perhexiline maleate, rottlerin, chaetocin, thioridazine, radicicol, salermide, dimercaptopropanol, everolimus, raltitrexed, manumycin A, wortmannin, 6 mercaptopurine, Palbociclib, tiopronin, succimer, camptothecin, captopril, R406, AZD-7762, SB 218078, Crizotinib, LDN-193189, Daunorubicin, Mitomycin C, Geldanamycin, Luminepib, BMS-387032, CGP-60474, Alvocidib, PD-0325901, PD-184352, PD 98059, AZD-8330, Dovidtinib, BIBU 1361 Dihydrochloride, Canertinib, TWS119, AZD-8055, Torin-1, Torin-2, WYE-123132, PP 2, WZ-3105, HY-10247, Auranofin, 16-hydroxytiptolide, Withaferin-a, AS605240, ZSTK-474, Trichostatin A, PP-110, Akt inhibitor X, BML-257, A443654, Colforsin, P5172, Coumermycin A1, RO8181, Tropisetron, Tofacitinib, Atracytlenolide, FLLL32, Zotiraciclib, Upadacitinib, Cerdulatinib, Baricitinib, Peficitinib, Levetiracetam, and Sinomenine.

The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration. Compounds can be synthesized by a variety of methods known in the art.

Compounds are revealed to protect against hair cell apoptosis. Compounds are identified as acting against hair cell loss in animals by the models and data presented. Models reveal properties necessary for an otoprotective compound such as high efficacy against hair cell loss.

Compounds are revealed to have high efficacy and high affinity in mouse and zebrafish models used to demonstrate protection against hair cell loss. The lateral-line neuromasts of zebrafish are a valuable model for testing compounds protective against cisplatin toxicity in vivo, as their HCs are considered homologous to those in the mammalian inner ear and are readily accessible to drugs in vivo. Teitz et al., J. Exp. Med. 2; 215(4):1187-1203 (2018) Mouse models involving HEI-OC1 have shown effective in validating therapeutic uses of compounds against hearing loss due to cisplatin, noise, antibiotics and aging. Teitz et al., J. Exp. Med. 2; 215(4):1187-1203 (2018).

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions include the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques. The pharmaceutical compositions of the present invention include a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The carrier can be a solvent or dispersion medium containing, for example, water, ethanol, polyol (e.g., glycerol, propylene glycol and liquid polyethylene glycol), vegetable oils, and suitable mixtures thereof.

The following are intended to be exemplary of how one of ordinary skill in the art could make and evaluate the claimed methods, compounds, compositions, articles, and/or devices, and are not intended to limit the scope of the invention.

Figure 2A:
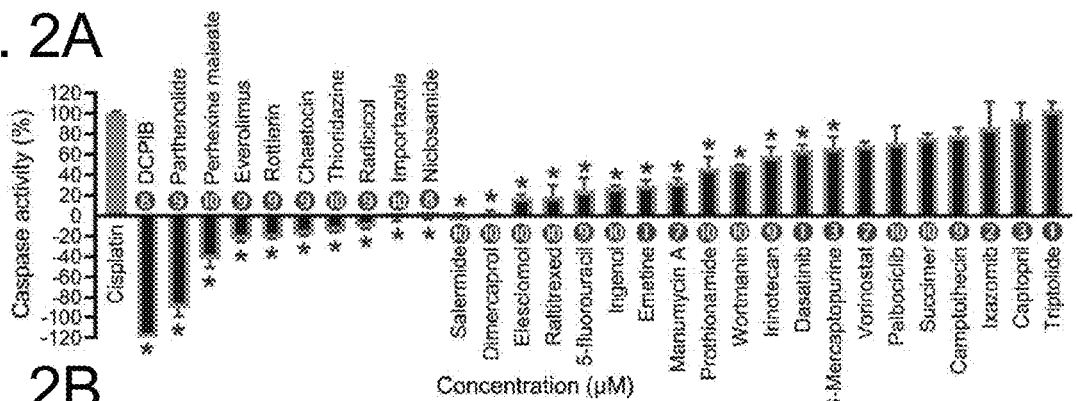
FIG. 2A shows the lowest level of caspase-3/7 activity in HEI-OC1 cells treated with Cisplatin (50 µM) and experimental compounds. Raw caspase reads were normalized to caspase activity in cells treated with Cisplatin/DMSO and cells treated with 1% DMSO. Niclosamide, was shown to reduce caspase activity to comparable levels as control cells at a dose of 4.4 µM. Data are shown as mean±standard error (n=3 wells per treatment). *P<0.05 (One Way ANOVA).

Now referring to FIG. 2A, compounds protect from cisplatin toxicity in the mouse inner ear cell line. House Ear Institute-Organ of Corti 1 (HEI-OC1) cells (House Research Institute) were maintained in high-glucose Dulbecco's modified Eagle medium supplemented with 10% fetal bovine serum (Life Technologies, USA) at 33° C. and 10% CO2 as previously described (Kalinec et al., 2003). Cells were seeded at 8,000 cells/well in 96 well plates and left to attach overnight. For the drug screening, HEI-OC1 cells were pretreated with 31 drug candidates at concentrations ranging from 2 nM to 40 µM one hour before receiving cisplatin. The cisplatin dose (50 µM) was based on our previously published dose response curve. The cells were co-incubated with cisplatin and drug candidates for an additional 19 hours prior to Caspase-Glo 3/7 assay (Promega, Madison, WI) as previously shown. Additionally, DMSO-only cells, and kenpaullone-treated cells were used as positive controls to validate our results. The DMSO concentration in drug preparation was adjusted to 0.1% v/v and it was verified that 0.5% DMSO had no effect on the cell death kinetics (Hall et al., 2014). Results of the assay were run in triplicate and normalized to cisplatin-only and media-only controls. The percent caspase activity was used to determine the relative protective effect of each compound. The luminescence detection representing caspase activity in each well was obtained using a Cytation Hybrid Multi-Mode Reader (Biotek, Winooski, VT, USA). The percent protection of the cells was calculated using caspase 3/7 readouts and the following formula:

$$\text{Percent protection} = 100 - \frac{\text{Drug and cisplatin exposed} - \text{Control}}{\text{Cisplatin exposed} - \text{Control}} \times 100$$

Figure 2B:
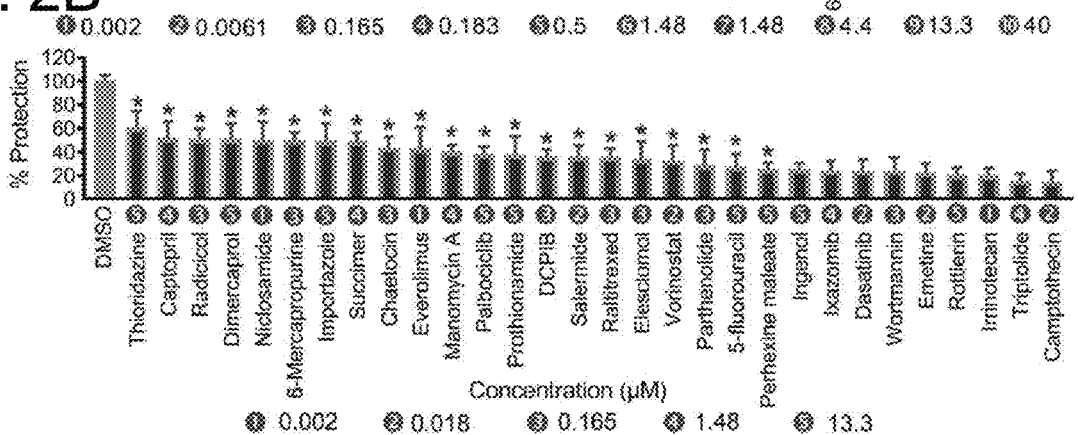
FIG. 2B shows the highest level of protection in zebrafish treated with Cisplatin and experimental compounds quantified by neuromast count hair cell count. Quantification of the HCs at SO3 (supraorbital line neuromast) and O1-2 (Otic line neuromasts) revealed significantly reduced Cisplatin damage in zebrafish HCs pretreated with 0.002 µM Niclosamide, (n=5 to 8 per group, One Way ANOVA).

Now referring to FIG. 2B, Highest level of protection in zebrafish treated with Cisplatin and experimental compounds quantified by neuromast count hair cell count. Quantification of the HCs at SO3 (supraorbital line neuromast) and O1-2 (Otic line neuromasts) revealed significantly reduced Cisplatin damage in zebrafish HCs pretreated with 0.002 µM Niclosamide, (n=5 to 8 per group, One Way ANOVA).

Figure 3A:
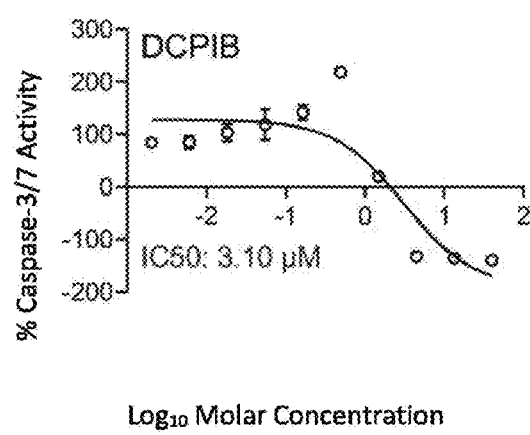
FIG. 3A shows DCPIB protects against CIHL.

Now referring to FIG. 3A, DCPIB protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with DCPIB reached 0% caspase activity at a dosage of ~4.4 µM. FIG. 3A. Additionally, DCPIB had a relatively low calculated $IC_{50}$ of 3.10 µM. FIG. 2A.

Figure 3B:
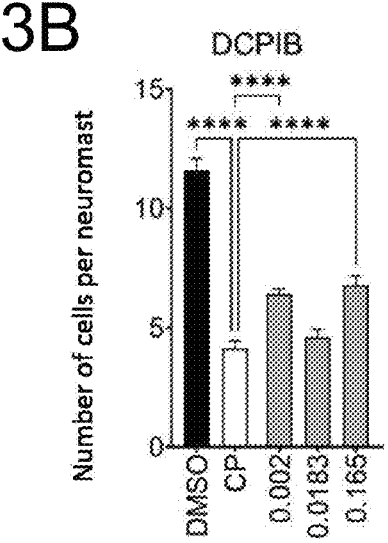
FIG. 3B shows DCPIB protects against cisplatin ototoxicity.

Now referring to FIG. 3B, DCPIB protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with DCPIB at 0.002, 0.018, 0.165, 1.48, and 13.3 µM for 1 hour followed by co-incubation with 400 µM cisplatin for 4 hours. DCPIB showed protection against CIHL at the various doses shown.

Figure 4A:
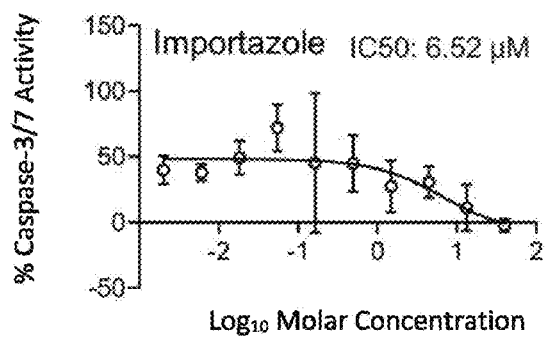
FIG. 4A shows importazole protects against CIHL.

Now referring to FIG. 4A, importazole protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with importazole reached 0% caspase activity at a dosage of ~40 µM. FIG. 2A. Additionally, importazole had a relatively low calculated $IC_{50}$ of 6.52 µM. FIG. 4A.

Figure 4B:
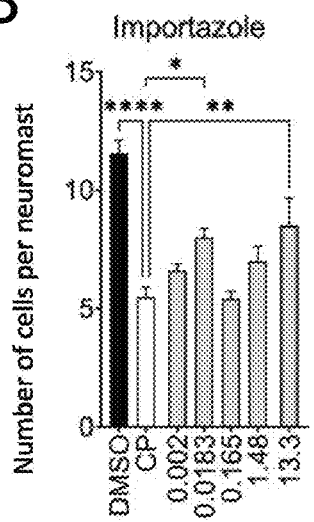
FIG. 4B shows importazole protects against cisplatin ototoxicity.

Now referring to FIG. 4B, importazole protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with importazole at 0.002, 0.018, 0.165, 1.48, and 13.3 µM for 1 hour followed by co-incubation with 400 µM cisplatin for 4 hours. Importazole showed protection against CIHL at the various doses shown.

Figure 4C:
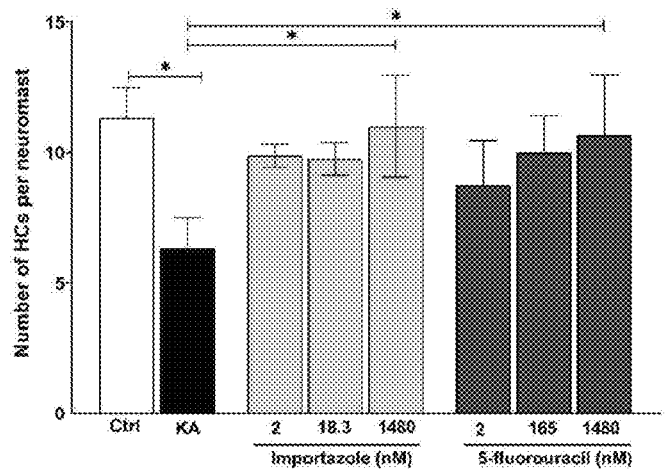
FIG. 4C shows importazole and 5-fluorouracil protect hair cells from excitotoxic damage in zebrafish. (*P<0.05, one-way ANOVA.)

FIG. 4C shows a comparison of importazole and 5-fluorouracil protecting hair cells from excitotoxic damage in zebrafish. (*P<0.05, one-way ANOVA.)

Figure 5A:
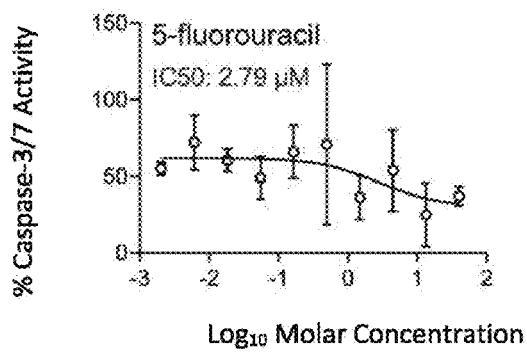
FIG. 5A shows 5-fluorouracil (5FU) protects against CIHL.

Now referring to FIG. 5A, 5-fluorouracil (5FU) protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with 5-fluorouracil reached ~30% caspase activity at a dosage of ~13.3 µM. FIG. 2A. Additionally, 5-fluorouracil had a relatively low calculated $IC_{50}$ of 2.79 µM. FIG. 5A.

Figure 5B:
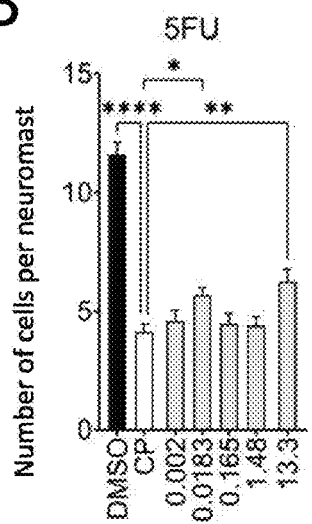
FIG. 5B shows 5-fluorouracil protects against cisplatin ototoxicity.

Now referring to FIG. 5B, 5-fluorouracil protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panel. Zebrafish were incubated with 5-fluorouracil at 0.002, 0.018, 0.165, 1.48, and 13.3 µM for 1 hour followed by co-incubation with 400 µM cisplatin for 4 hours. 5-fluorouracil showed protection against CIHL at the various doses shown.

Figure 6A:
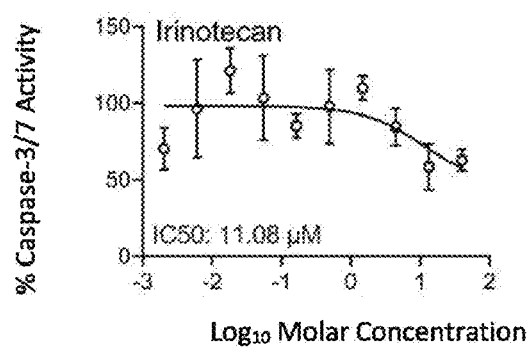
FIG. 6A shows irinotecan protects against CIHL.
Figure 6B:
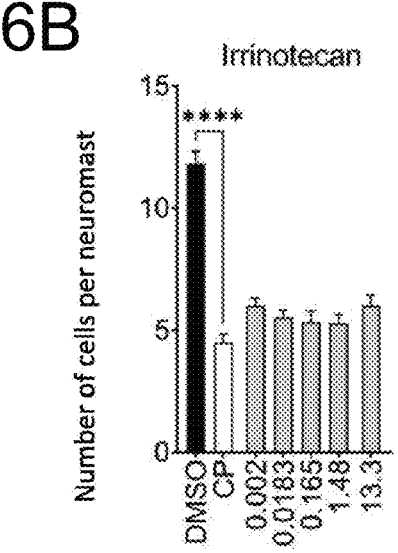
FIG. 6B shows irinotecan protects against cisplatin ototoxicity.

Now referring to FIG. 6A, irinotecan protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with irinotecan reached ~60% caspase activity at a dosage of ~13.3 µM. FIG. 2A. Additionally, irinotecan had a relatively low calculated $IC_{50}$ of 11.08 µM. FIG. 6A Now referring to FIG. 6B, irinotecan protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with irinotecan at 0.002, 0.018, 0.165, 1.48, and 13.3 µM for 1 hour followed by co-incubation with 400 µM cisplatin for 4 hours. Irinotecan showed protection against CIHL at the various doses shown.

Figure 7A:
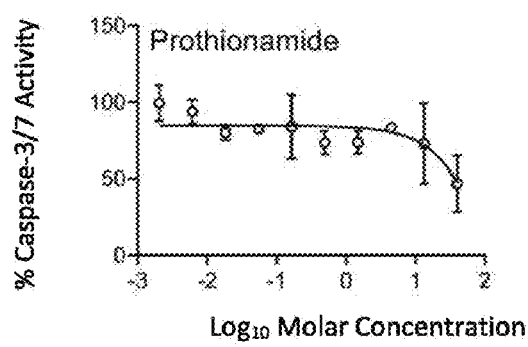
FIG. 7A shows prothionamide protects against CIHL.

Now referring to FIG. 7A, prothionamide protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with prothionamide reached ~50% caspase activity at a dosage of ~40 µM. FIG. 2A. Additionally, parthenolide had a relatively low calculated $IC_{50}$ of ~40 µM. FIG. 7A.

Figure 7B:
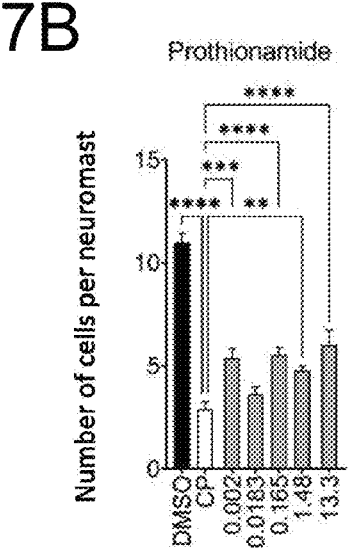
FIG. 7B shows prothionamide protects against cisplatin ototoxicity.

Now referring to FIG. 7B, prothionamide protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with prothionamide at 0.002, 0.018, 0.165, 1.48, and 13.3 µM for 1 hour followed by co-incubation with 400 µM cisplatin for 4 hours. Prothionamide showed protection against CIHL at the various doses shown.

Now referring to FIG. 8A, parthenolide protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with parthenolide reached 0% caspase activity at a dosage of ~13.3 µM. FIG. 2A. Additionally, parthenolide had a relatively low calculated $IC_{50}$ of 21 µM. FIG. 8A.

Now referring to FIG. 8B, parthenolide protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with parthenolide at 0.002, 0.018, 0.165, 1.48, and 13.3 µM for 1 hour followed by co-incubation with 400 µM cisplatin for 4 hours. Parthenolide showed protection against CIHL at the various doses shown.

Now referring to FIG. 9A, perhexiline maleate protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with perhexiline maleate reached 0% caspase activity at a dosage of ~40 µM. FIG. 1A. Additionally, perhexine maleate had a relatively low calculated $IC_{50}$ of X µM. FIG. 9A.

Now referring to FIG. 9B, perhexiline maleate protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with perhexiline maleate at 0.002, 0.018, 0.165, 1.48, and 13.3 µM for 1 hour followed by co-incubation with 400 µM cisplatin for 4 hours. Perhexiline maleate showed protection against CIHL at the various doses shown.

Now referring to FIG. 10A, everolimus protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}s$ were calculated. HEI-OC1 cells treated with everolimus reached 0% caspase activity at a dosage of ~13.3 µM. FIG. 2A. Additionally, everolimus had a relatively low calculated $IC_{50}$ of 6.6 µM. FIG. 10A.

Now referring to FIG. 10B, everolimus protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with everolimus at 0.002, 0.018, 0.165, 1.48, and 13.3 µM for 1 hour followed by co-incubation with 400 µM cisplatin for 4 hours. Everolimus showed protection against CIHL at the various doses shown.

Now referring to FIG. 11A, rottlerin protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with rottlerin reached 0% caspase activity at a dosage of ~13.3 µM. FIG. 2A. Additionally, rottlerin had a relatively low calculated $IC_{50}$ of 7.36 µM. FIG. 11A.

Now referring to FIG. 11B, rottlerin protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with rottlerin at 0.002, 0.018, 0.165, 1.48, and 13.3 µM for 1 hour followed by co-incubation with 400 µM cisplatin for 4 hours. Rottlerin showed protection against CIHL at the various doses shown.

Figure 12A:
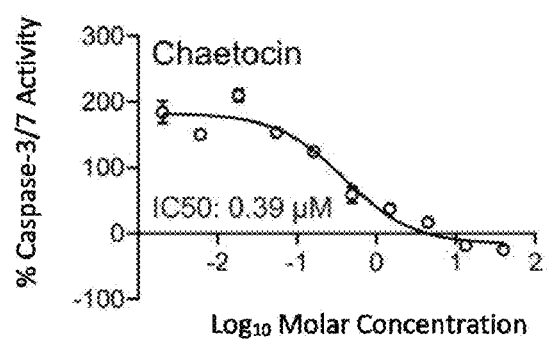
FIG. 12A shows chaetocin protects against CIHL.

Now referring to FIG. 12A, chaetocin protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with chaetocin reached 0% caspase activity at a dosage of ~13.3 µM. FIG. 2A. Additionally, chaetocin had a relatively low calculated $IC_{50}$ of 0.39 µM. FIG. 12A.

Figure 12B:
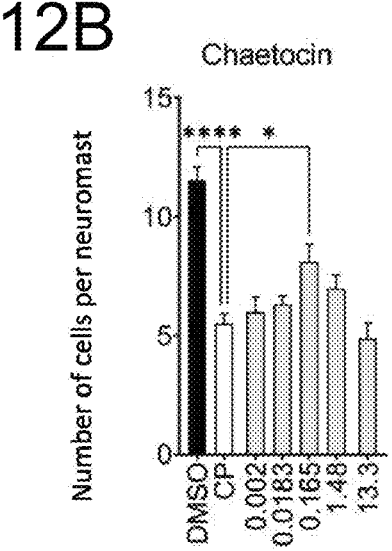
FIG. 12B shows chaetocin protects against cisplatin ototoxicity.

Now referring to FIG. 12B, chaetocin protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with chaetocin at 0.002, 0.018, 0.165, 1.48, and 13.3 µM for 1 hour followed by co-incubation with 400 µM cisplatin for 4 hours. Chaetocin showed protection against CIHL at the various doses shown.

Figure 13A:
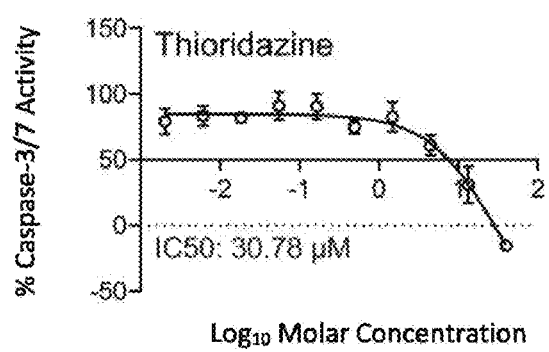
FIG. 13A shows thioridazine protects against CIHL.

Now referring to FIG. 13A, thioridazine protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with thioridazine reached 0% caspase activity at a dosage of ~40 µM. FIG. 2A. Additionally, thioridazine had a relatively low calculated $IC_{50}$ of 30.78 µM. FIG. 13A.

Figure 13B:
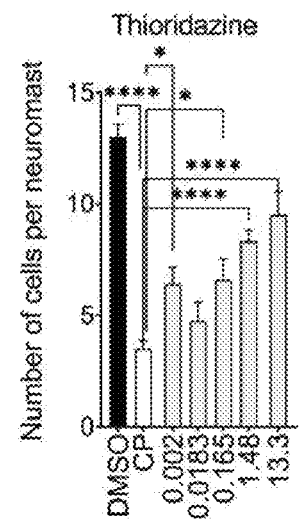
FIG. 13B shows thioridazine protects against cisplatin ototoxicity.

Now referring to FIG. 13B, thioridazine protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with thioridazine at 0.002, 0.018, 0.165, 1.48, and 13.3 µM for 1 hour followed by co-incubation with 400 µM cisplatin for 4 hours. Thioridazine showed protection against CIHL at the various doses shown.

Figure 14A:
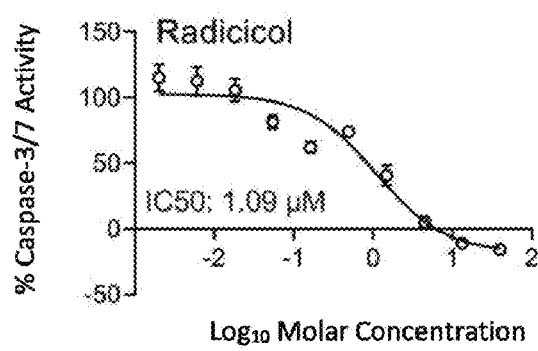
FIG. 14A shows radicicol protects against CIHL.

Now referring to FIG. 14A, radicicol protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with radicicol reached 0% caspase activity at a dosage of ~13.3 µM. FIG. 2A. Additionally, radicicol had a relatively low calculated $IC_{50}$ of 1.09 µM. FIG. 14A.

Figure 14B:
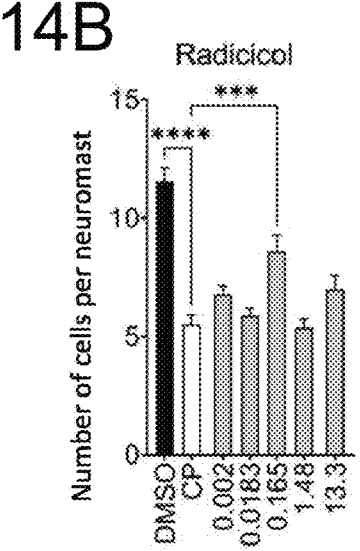
FIG. 14B shows radicicol protects against cisplatin ototoxicity.

Now referring to FIG. 14B, radicicol protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with radicicol at 0.002, 0.018, 0.165, 1.48, and 13.3 µM for 1 hour followed by co-incubation with 400 µM cisplatin for 4 hours. Radicicol showed protection against CIHL at the various doses shown.

Figure 15A:
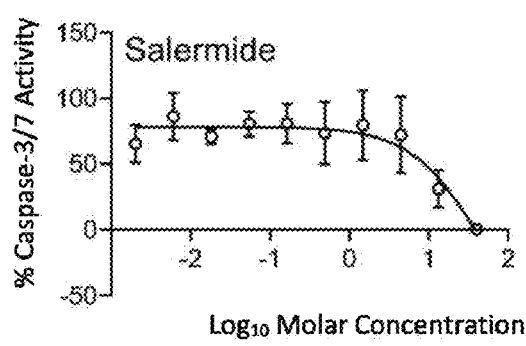
FIG. 15A shows salermide protects against CIHL.

Now referring to FIG. 15A, salermide protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with salermide reached 0% caspase activity at a dosage of ~40 µM. FIG. 2A. Additionally, salermide had a relatively low calculated $IC_{50}$ of ~15 µM. FIG. 15A.

Figure 15B:
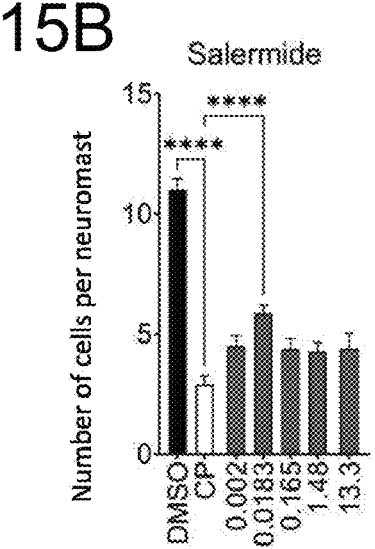
FIG. 15B shows salermide protects against cisplatin ototoxicity.

Now referring to FIG. 15B, salermide protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with salermide at 0.002, 0.018, 0.165, 1.48, and 13.3 µM for 1 hour followed by co-incubation with 400 µM cisplatin for 4 hours. Salermide showed protection against CIHL at the various doses shown.

Figure 16A:
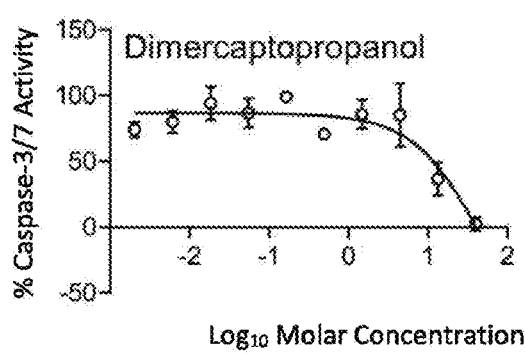
FIG. 16A shows dimercaptopropanol protects against CIHL.

Now referring to FIG. 16A, dimercaptopropanol protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with dimercaptopropanol reached 0% caspase activity at a dosage of ~40 µM. FIG. 2A. Additionally, dimercaptopropanol had a relatively low calculated $IC_{50}$ of ~15 µM. FIG. 16A.

Figure 16B:
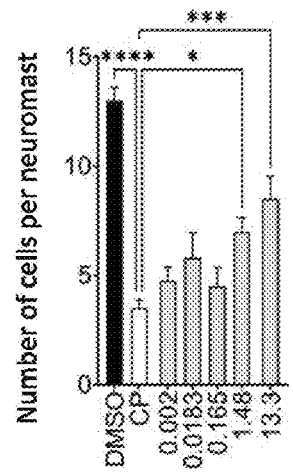
FIG. 16B shows dimercaptopropanol protects against cisplatin ototoxicity.

Now referring to FIG. 16B, dimercaptopropanol protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with dimercaptopropanol at 0.002, 0.018, 0.165, 1.48, and 13.3 µM for 1 hour followed by co-incubation with 400 µM cisplatin for 4 hours. Dimercaptopropanol showed protection against CIHL at the various doses shown.

Figure 17A:
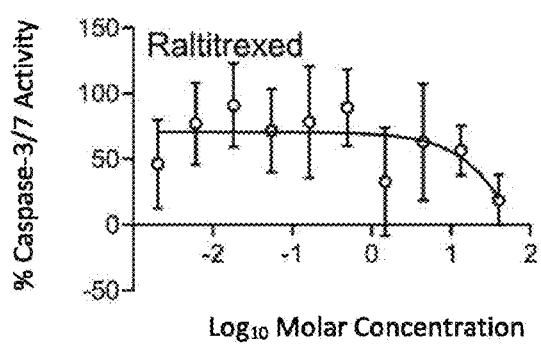
FIG. 17A shows raltitrexed protects against CIHL.

Now referring to FIG. 17A, raltitrexed protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with raltitrexed reached ~20% caspase activity at a dosage of ~40 µM. FIG. 2A. Additionally, raltitrexed had a relatively low calculated $IC_{50}$ of ~15 µM. FIG. 17A.

Figure 17B:
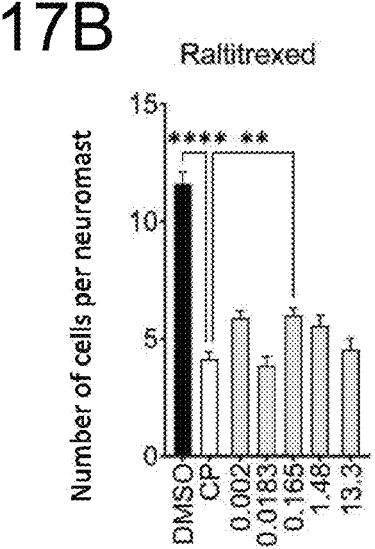
FIG. 17B shows raltitrexed protects against cisplatin ototoxicity.

Now referring to FIG. 17B, raltitrexed protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with raltitrexed at 0.002, 0.018, 0.165, 1.48, and 13.3 µM for 1 hour followed by co-incubation with 400 µM cisplatin for 4 hours. Raltitrexed showed protection against CIHL at the various doses shown.

Figure 18A:
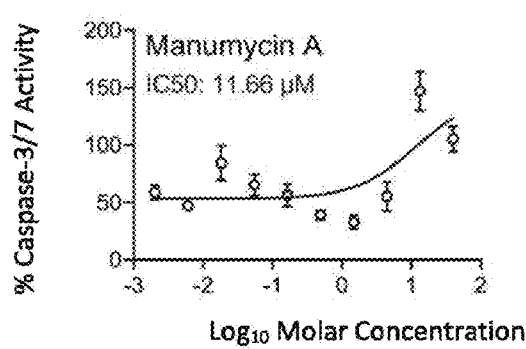
FIG. 18A shows manumycin A protects against CIHL.

Now referring to FIG. 18A, manumycin A protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with manumycin A reached ~35% caspase activity at a dosage of ~1.48 µM. FIG. 2A. Additionally, manumycin A had a relatively low calculated $IC_{50}$ of 11.66 µM. FIG. 18A.

Figure 18B:
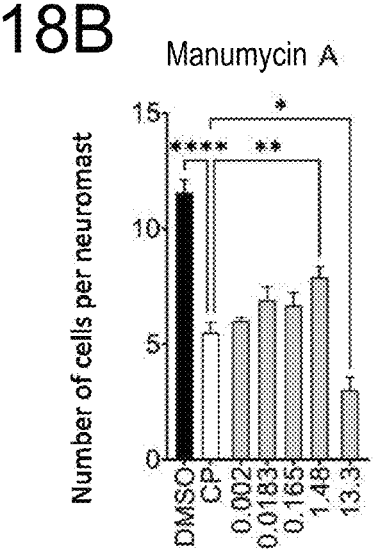
FIG. 18B shows manumycin A protects against cisplatin ototoxicity.

Now referring to FIG. 18B, manumycin A protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with manumycin A at 0.002, 0.018, 0.165, 1.48, and 13.3 µM for 1 hour followed by co-incubation with 400 µM cisplatin for 4 hours. Manumycin A showed protection against CIHL at the various doses shown.

Figure 19A:
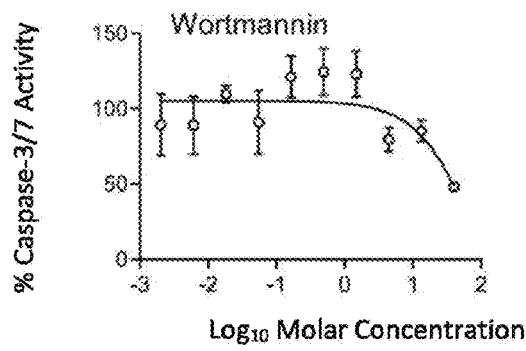
FIG. 19A shows wortmannin protects against CIHL.

Now referring to FIG. 19A, wortmannin protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with wortmannin reached ~50% caspase activity at a dosage of ~40 µM. FIG. 2A. Additionally, wortmannin had a relatively low calculated $IC_{50}$ of ~40 µM. FIG. 19A.

Figure 19B:
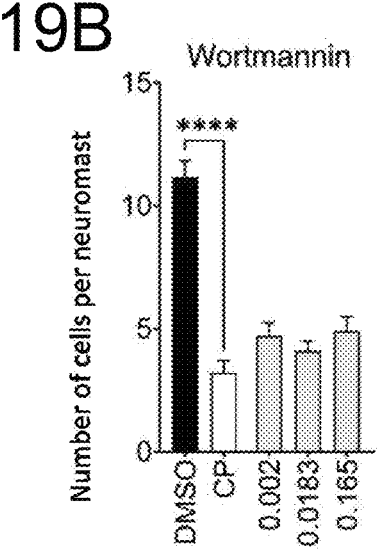
FIG. 19B shows wortmannin protects against cisplatin ototoxicity.

Now referring to FIG. 19B, wortmannin protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with wortmannin at 0.002, 0.018, 0.165, 1.48, and 13.3 µM for 1 hour followed by co-incubation with 400 µM cisplatin for 4 hours. Wortmannin showed protection against CIHL at the various doses shown.

Figure 20A:
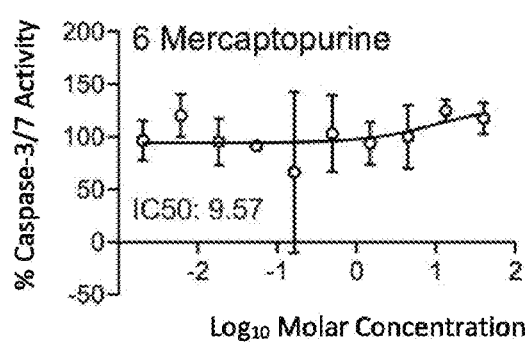
FIG. 20A shows 6 mercaptopurine protects against CIHL.
Figure 21A:
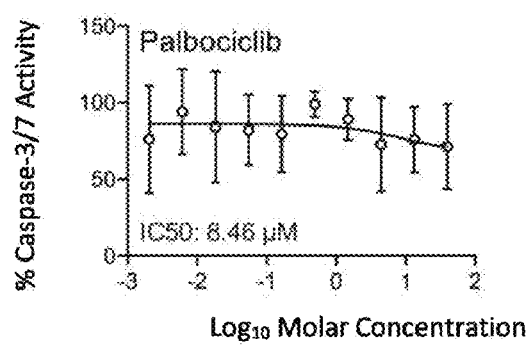
FIG. 21A shows palbociclib protects against CIHL.

Now referring to FIG. 20A, 6 mercaptopurine protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with 6 mercaptopurine reached ~70% caspase activity at a dosage of ~0.165 µM. FIG. 2A. Additionally, 6 mercaptopurine had a relatively low calculated $IC_{50}$ of 9.57 µM. FIG. 21A.

Figure 20B:
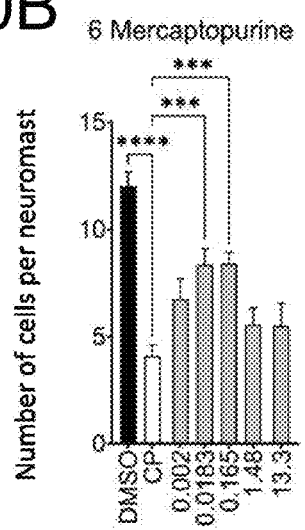
FIG. 20B shows 6 mercaptopurine protects against cisplatin ototoxicity.

Now referring to FIG. 20B, 6 mercaptopurine protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with 6 mercaptopurine at 0.002, 0.018, 0.165, 1.48, and 13.3 µM for 1 hour followed by co-incubation with 400 µM cisplatin for 4 hours. 6 mercaptopurine showed protection against CIHL at the various doses shown.

Figure 22A:
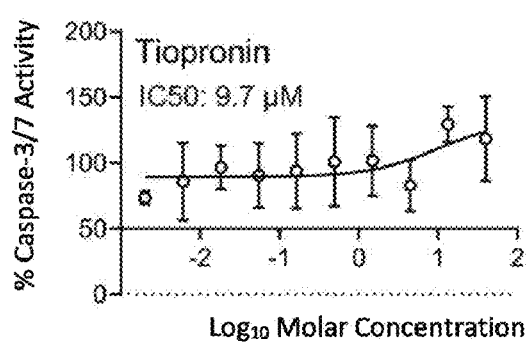
FIG. 22A shows tiopronin protects against CIHL.

Now referring to FIG. 21A, palbociclib protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with palbociclib reached ~80% caspase activity at a dosage of ~40 µM. FIG. 2A. Additionally, palbociclib had a relatively low calculated $IC_{50}$ of 8.46 µM. FIG. 22A.

Figure 21B:
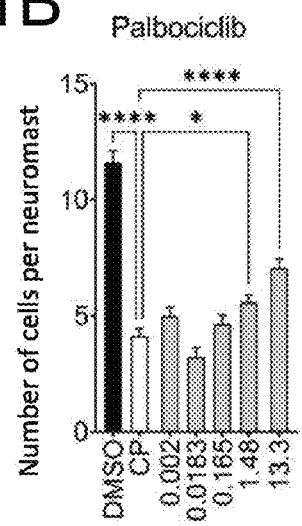
FIG. 21B shows palbociclib protects against cisplatin ototoxicity.

Now referring to FIG. 21B, palbociclib protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with palbociclib at 0.002, 0.018, 0.165, 1.48, and 13.3 µM for 1 hour followed by co-incubation with 400 µM cisplatin for 4 hours. Palbociclib showed protection against CIHL at the various doses shown.

Figure 22B:
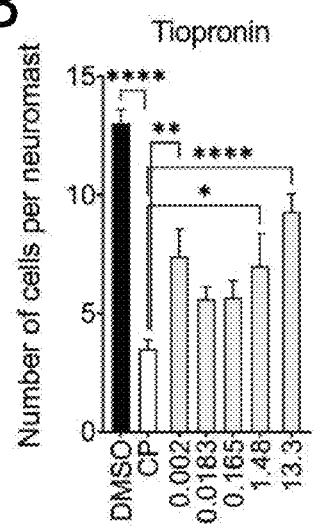
FIG. 22B shows tiopronin protects against cisplatin ototoxicity.

Now referring to FIG. 22A, tiopronin protects against CIHL. Caspase activity was measured using Caspase-Glo 3/7 assay and then the results were calculated as percentage of protection as an indicator of cell survival viability. Additionally, tiopronin had a relatively low calculated $IC_{50}$ of 9.7 µM. FIG. 2A. Now referring to FIG. 22B, tiopronin protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with tiopronin at 0.002, 0.018, 0.165, 1.48, and 13.3 µM for 1 hour followed by co-incubation with 400 µM cisplatin for 4 hours. Tiopronin showed protection against CIHL at the various doses shown.

Figure 23A:
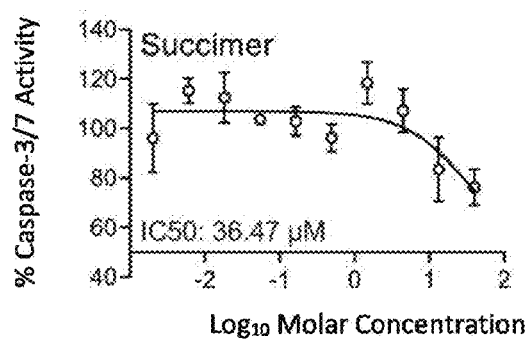
FIG. 23A shows succimer protects against CIHL.

Now referring to FIG. 23A, succimer protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with succimer reached ~80% caspase activity at a dosage of ~40 µM. FIG. 2A. Additionally, succimer had a relatively low calculated $IC_{50}$ of 36.47 µM. FIG. 23A.

Figure 23B:
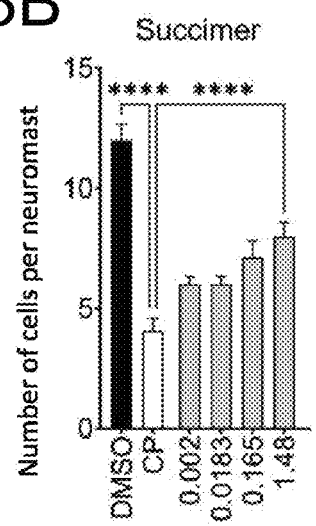
FIG. 23B shows succimer protects against cisplatin ototoxicity.

Now referring to FIG. 23B, succimer protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with succimer at 0.002, 0.018, 0.165, 1.48, and 13.3 µM for 1 hour followed by co-incubation with 400 µM cisplatin for 4 hours. Succimer showed protection against CIHL at the various doses shown.

Figure 24A:
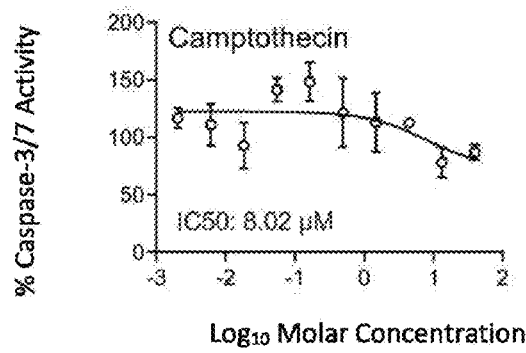
FIG. 24A shows camptothecin protects against CIHL.

Now referring to FIG. 24A, camptothecin protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with camtpothecin reached ~80% caspase activity at a dosage of ~13.3 µM. FIG. 2A. Additionally, camptothecin had a relatively low calculated $IC_{50}$ of 8.02 µM. FIG. 24A.

Figure 24B:
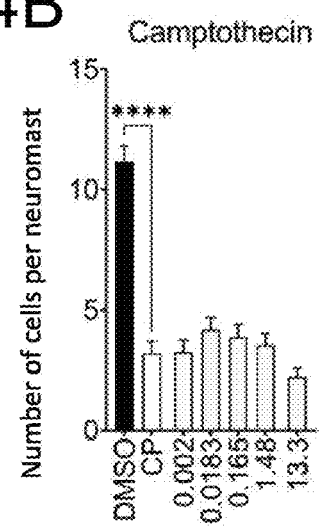
FIG. 24B shows camptothecin protects against cisplatin ototoxicity.

Now referring to FIG. 24B, camptothecin protects against cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with camptothecin at 0.002, 0.018, 0.165, 1.48, and 13.3 µM for 1 hour followed by co-incubation with 400 μM cisplatin for 4 hours. Camptothecin showed protection against CIHL at the various doses shown.

Figure 25A:
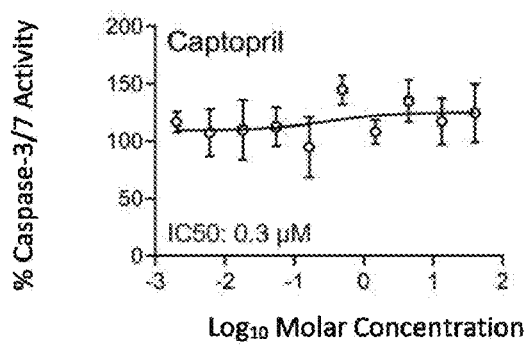
FIG. 25A shows captopril protects against CIHL.

Now referring to FIG. 25A, captopril protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with captopril reached ~85% caspase activity at a dosage of ~0.165 μM. FIG. 2A. Additionally, captopril had a relatively low calculated $IC_{50}$ of 0.3 μM. FIG. 25A.

Figure 25B:
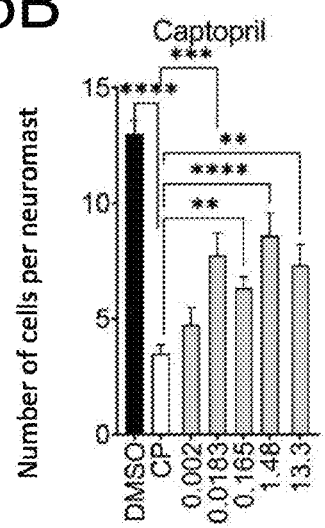
FIG. 25B shows captopril protects against cisplatin ototoxicity.

Now referring to FIG. 25B, captopril protects against cisplatin ototoxicity across multiple doses in zebrafish (n=5-8 per group, One Way ANOVA). *$P<0.05$, data are shown as mean±standard error (n=5 per group). *$P<0.05$, data shown as mean±standard error in all panels. Zebrafish were incubated with captopril at 0.002, 0.018, 0.165, 1.48, and 13.3 μM for 1 hour followed by co-incubation with 400 μM cisplatin for 4 hours. Captopril showed protection against CIHL at the various doses shown.

All publications, patents and patent applications mentioned in this specification are herein incorporated by reference to the same extent as if each individual publication, patent or patent application was specifically and individually indicated to be incorporated by reference.

Teitz T, Fang J, Goktug A N, et al. CDK2 inhibitors as candidate therapeutics for cisplatin- and noise-induced hearing loss. J Exp Med 2018; 215:1187-203. PMID: 29514916.

Kalinec G M, Webster P, Lim D J, Kalinec F. A cochlear cell line as an in vitro system for drug ototoxicity screening. Audiol Neurootol 2003; 8:177-89. PMID: 12811000.

While the invention has been described with reference to details of the illustrated embodiments, these details are not intended to limit the scope of the invention as defined in the appended claims. The embodiment of the invention in which exclusive property or privilege is claimed is defined as follows:

What is claimed:

1. A method to prevent or treat hearing loss caused by a chemotherapeutic agent, comprising: administering chaetocin.

2. The method of claim 1, comprising protecting the inner ear cells from death caused by a chemotherapeutic agent.

3. The method of claim 2, wherein the chemotherapeutic agent cisplatin.

* * * * *